United States Patent [19]

Calcagno et al.

[11] 4,341,913

[45] Jul. 27, 1982

[54] PROCESS FOR THE PRODUCTION OF CUMENE

[75] Inventors: Benedetto Calcagno, Milan; Emanuele Sartorio, Messina; Claudio Divo, Saronno; Luigi Verde, Busto Arsizio, all of Italy

[73] Assignee: Euteco Impianti S.p.A., Milan, Italy

[21] Appl. No.: 217,736

[22] Filed: Dec. 19, 1980

[30] Foreign Application Priority Data

Dec. 19, 1980 [IT] Italy ............................. 28220 A/79

[51] Int. Cl.³ ............................................. C07C 2/68
[52] U.S. Cl. .................................. 585/449; 585/466
[58] Field of Search ............................... 585/466, 449

[56] References Cited

U.S. PATENT DOCUMENTS

| | | | |
|---|---|---|---|
| 2,120,702 | 6/1938 | Ipatieff et al. | 585/529 |
| 2,613,188 | 10/1952 | Mavity | 585/466 |
| 3,813,451 | 5/1974 | Canfield et al. | 585/466 |
| 4,051,191 | 9/1977 | Ward | 585/466 |
| 4,108,914 | 8/1978 | Gewartowski | 585/466 |

*Primary Examiner*—Curtis R. Davis
*Attorney, Agent, or Firm*—Sughrue, Mion, Zinn, Macpeak & Seas

[57] ABSTRACT

Production of cumene by alkylation of benzene with propylene on a solid phosphoric acid catalyst, using a first step with a plurality of catalyst beds in series and a second step with a single catalyst bed, using an overall benzene/propylene molar ratio of at least 6:1, continuously delivering the benzene to the first bed, continuously delivering a series of streams of liquid propylene respectively to the first bed and, in the form of a cold stream, between each pair of contiguous beds, and using a benzene/propylene molar ratio higher than 16:1 at the inlet of each bed of the first step, and higher than 25:1 at the inlet of the bed of the second step.

9 Claims, 1 Drawing Figure

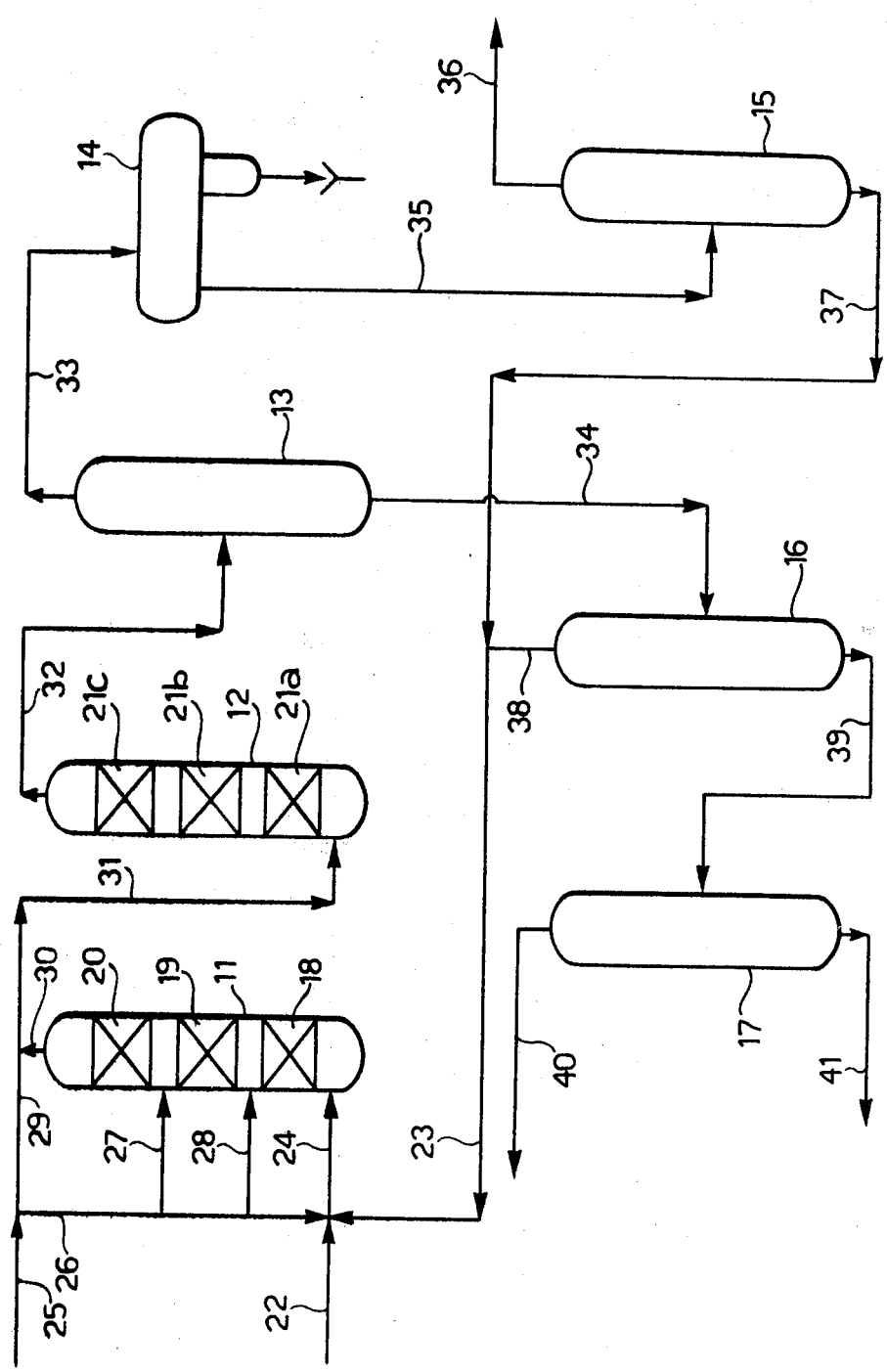

PROCESS FOR THE PRODUCTION OF CUMENE

The present invention relates to improvements in the process for the production of cumene from benzene and propylene on solid phosphoric acid catalysts.

Cumene (or isopropylbenzene) is a valuable product, generally used as an intermediate in the synthesis of other chemical compounds, especially in the production of phenol and acetone via cumene hydroperoxide.

In the known art, the alkylation of benzene with propylene is carried out either in the gaseous or in the liquid phase in the presence of suitable catalysts, as described by S. H. Mc.Allister et al. in "Chemical Engineering Progress", Vol. 43, No. 4 (1947), at pages 189–196. The catalysts generally used are based on solid phosphoric acid, described for example in British Pat. No. 836,539 and U.S. Pat. Nos. 2,120,702 and 2,613,188, as well as in the article mentioned above.

In the known industrial processes, liquid benzene and liquid propylene are usually fed to a reactor which contains the solid catalyst in the form of a fixed bed or in the form of a series of fixed beds. In order to minimize the formation of poly-isopropyl-benzene by-products (di-isopropylbenzene and tri-isopropylbenzene) an excess of benzene with respect to the propylene is usually maintained in the feed, thus to reduce also the quantity of oligomers of propylene, such as dimers and trimers.

The formation of said by-products is promoted by the formation of hot points in the catalytic bed, as a result of the exothermal nature of the alkylation reaction. In said hot points a gaseous phase may form, in which the concentration of propylene is high. Attempts have been made to overcome this drawback by arranging the catalyst in the form of a series of fixed beds and feeding partly the cold reagents (benzene and propylene) between each pair of contiguous beds, as described, for example, in U.S. Pat. No. 3,813,451.

This expedient certainly makes easier the control of the exothermal nature of reaction, but does not permit the best ratio between benzene and propylene to be maintained in the reaction medium. As a result, the quantity of by-products, especially polyalkylbenzenes, is relatively high.

It has now been found that the drawbacks of the known art can be overcome, and that it is possible to produce cumene from benzene and propylene by operating in the liquid phase and on solid phosphoric acid catalysts, by means of a simple and convenient process in which the conversion into polyalkylbenzenes and propylene oligomers is reduced to very low values.

More particularly, the present invention provides a continuous process for the production of cumene by alkylation of benzene with propylene on a solid phosphoric acid catalyst, said process being characterized by:

using two reaction steps in series, the first step being carried out in a plurality of catalytic beds in series and the second step in a catalytic bed of volume equal or similar to the overall volume of the catalytic beds of the first step;

operating in said first and second steps in the liquid phase, at a temperature of from 170° to 270° C. and under a pressure of from 30 to 50 Kg/sq. cm.;

using an overall benzene/propylene molar ratio of at least 6:1, continuously delivering the whole of the liquid benzene to the first catalytic bed of the first step, continuously delivering a series of streams of liquid propylene to the first catalytic bed of the first step and, in the form of a cold stream, between each pair of contiguous beds in the first and second steps, in such amounts that the benzene/propylene molar ratio be higher than about 16:1 at the inlet of each individual catalytic bed of the first step, and higher than about 25:1 at the inlet of the catalytic bed of the second step;

recovering cumene from the reaction products discharged from the second step.

The present invention is essentially based on the finding that the more uniform the composition and temperature of the reaction medium, the more favourable is the course of the catalytic alkylation reaction of benzene with propylene as regards the formation of by-products.

Conditions similar to the optimum conditions indicated above are achieved according to the present invention by delivering decreasing portions of the overall amount of propylene upstream of each catalytic bed. By using this expedient the variation in concentration of free propylene is low along each catalytic bed, as is also the gradient of temperature, the latter being on an average of the order of 15°–20° C. along the catalytic beds of the first step, and of the order of 10° C. along the catalytic bed of the second step.

In has also been ascertained that the use of relatively high residence times has a beneficial influence, in particular in the final reaction step in which the conversion of the free propylene present in the reaction medium is substantially brought to completion.

Therefore, the residence time in the completion step (second step) is preferably similar to that in the reaction step proper (first step).

Finally, by delivering the whole of the benzene to the first catalytic bed, the molar ratio between benzene and propylene is maintained at the highest possible values in each point of the reaction system, with consequent advantages deriving from the low formation of by-products.

Therefore, the process of the present invention is carried out in two reaction steps in series, using in the first of said steps a plurality of separate catalytic beds in series. The number of beds may generally range from 2 to 5, but preferably there are used three catalytic beds having the same or about the same volume.

Moreover, a characteristic of the present invention consists in using in the second step a single catalytic bed of volume equal, or about equal to the overall volume of the catalytic beds of the first step.

The alkylation catalysts suitable for the purpose are solid catalysts based on phosphoric acids, which are generally prepared by mixing acids in which phosphorus has a valency of 5, with a silicic material and treating the resulting mixture at elevated temperature. A preferred catalyst for the purposes of the present invention is prepared from diatomite having a silica content higher than 70% by weight. In particular, this support is heated at a temperature of the order of 250° C., until a specific surface area of 10–30 sq. m/g is achieved. The support is then mixed with the commercial complex product known as polyphosphoric acid, having a $P_2O_5$ content of the order of 85% by weight. Conveniently, one part by weight of support is mixed with two parts by weight of polyphosphoric acid, operating at ambient temperature or slightly above. After homogenization the mixture is formed into small cylinders, which typically have a diameter and a height of the order of 5–6 mm. The cylinders are then calcined at a temperature of the order of 300° C. for a period of 90-150 minutes.

The catalyst is arranged in the form of a fixed bed in reactors, generally tubular, according to the configuration already indicated.

In carrying out the process of the present invention, the whole of the benzene is delivered to the first catalytic bed of the first reaction step, whereas the propylene feed is divided into a plurality of streams, which are respectively delivered in the liquid form to the inlet of each individual catalytic bed. In each case the overall molar ratio between benzene and propylene in the feed is maintained at a value of at least 6:1. The maximum value of said ratio is not critical, but it is not convenient to exceed a limit of 10:1. The preferred values for said ratio are of the order of 8:1.

The division of the propylene feed between the catalytic beds of the first step is regulated in such a way that the benzene/propylene molar ratio at the inlet of each individual bed be higher than about 16:1, and preferably higher than 20:1, up to a maximum value of 25:1.

The conditions are also regulated in such a way that the molar ratio between benzene and propylene at the inlet of the second step be higher than about 25:1, and preferably of the order of 40:1. The maximum value of said ratio is not critical and is essentially dictated by economical considerations.

As regards the feed of propylene, said compound may be pure or substantially pure, or may contain inert compounds, such as hydrocarbons non-reactive under the operating conditions, in amounts not exceeding about 15% by weight.

The reaction temperature is generally from 170° to 270° C. and the operating pressure is such as to maintain the reaction medium in the liquid phase. The pressure is generally from 30 to 50 kg/sq. cm.

The exothermal nature of the reaction is controlled by setting a suitable inlet temperature to the first step, and by means of the injection of cold propylene stream (15°-50° C.) between each pair of continguous catalytic beds.

The space velocity, expressed as volume or liquid per volume or catalytic and per hour, is conveniently of the order of 0.3-1.4, preferably of the order of 0.4-0.9.

According to a typical embodiment of the process of the present invention, there is used an overall molar ratio between benzene and propylene of 8:1, operating with an inlet temperature of the reagents to the first catalytic bed of the order of 190°-205° C. and under the other conditions specified above.

In this manner the conversion with respect to propylene is typically higher than 80%, reckoned at the outlet of each individual catalytic bed of the first step, and the conversion of propylene at the outlet of the second step is complete or substantially complete. Moreover, the increases in temperature are of the order of 15°-20° C. in the catalytic beds of the first step and of the order of 10° C. in the catalytic bed of the second step.

Under these conditions the formation of by-products is of the order of 20-30 parts by weight for each 1000 parts by weight of cumene.

The separation of cumene from the reaction products discharged from the second step is carried out by conventional methods, such as distillation. The benzene recovered may be recycled and delivered to the first catalytic bed together with fresh benzene.

The following experimental example is illustrative and non-limitative for the invention.

EXAMPLE

There is used a solid phosphoric acid catalyst in the form of small cylinders with a size of 5.5 mm, obtained as described above in respect of the preferred embodiment of the preparation of the catalyst. This catalyst is arranged in the form of fixed beds in the first and the second reaction steps.

More particularly, with reference to the accompanying drawing, there are used a first step reactor 11 and a second step reactor 12. The catalyst is arranged in the reactor 11 in the form of three separate fixed beds in series shown in 18, 19 and 20. The beds 18, 19 and 20 have a similar volume of the order of 25-30 m$^3$. In reactor 12 the catalyst is arranged for the sake of convenience in the form of three beds 21a, 21b and 21c. However, owing to the absence of intermediate feedings, the functioning is that of a single bed having a volume equal to the overall volume of beds 18, 19 and 20 of the first step.

Fresh benzene is circulated through pipe 22 and mixed with the recycle benzene stream delivered through pipe 23. The weight ratio between the two streams is about 7:1. The two streams are combined and delivered through pipe 24 at a rate of 85,680 kg/h. The titre in benzene of said stream is about 96% by weight, the remaining percentage consisting essentially of cumene. Liquid propylene is delivered at a temperature of 30° C. through pipe 25 at a rate of 6,060 kg/h. This stream has a titre in propylene of about 92% by weight, the remaining percentage consiting essentially of propane.

The propylene stream of pipe 25 is delivered partially to reactor 11 (5,195 kg/h) through pipe 26, and the remaining part to reactor 12 (866 kg/h) through pipe 29.

The stream of pipe 26 is in turn divided into three streams which are delivered respectively through pipe 24 ahead of the catalytic bed 18, through pipe 28 ahead of the catalytic bed 19, and through pipe 27 ahead of catalytic bed 20. More particularly, propylene is delivered through pipe 24 at a rate of 2,000 kg/h to the inlet of catalytic bed 18, upon mixing with fresh benzene and recycle benzene and pre-heating of the combined streams. Water is also added to this stream in a quantity of 42 kg/h. The propylene streams of pipes 28 and 27 are delivered at a rate of 1,732 kg/h and respectively 1,463 kg/h.

The propylene stream of pipe 29 is mixed with the products issuing from reactor 11 through pipe 30. The resulting mixture is delivered to reactor 12 through pipe 31.

Reactors 11 and 12 are operated at a pressure of about 35-40 kg/sq.cm, thereby to maintain the reaction medium in the liquid phase. Under these conditions, the course of the alkylation reaction in the different catalytic beds is on an average the following:

catalytic bed 18: benzene/propylene molar ratio at the inlet of about 25:1 inlet temperature of 205° C., outlet temperature of 223° C., molar conversion of propylene of 80.8% and molar selectivity for cumene of 98% with respect to the converted propylene;

catalytic bed 19: benzene/propylene molar ratio at the inlet of about 23:1 inlet temperature of 218° C., outlet temperature of 238° C., overall molar conversion of propylene of 87.5% and overall molar selectivity for cumene of 96.2% with respect to the converted propylene;

catalytic bed 20: benzene/propylene molar ratio at the inlet of about 24:1; inlet temperature of 234° C., outlet temperature of 250° C., overall molar conversion of propylene of 91.3% and overall molar selectivity for cumene of 95% with respect to the converted propylene;

catalytic bed 21a-21b-21c: benzene/propylene molar ratio at the inlet of about 40:1, inlet temperature of 247° C., outlet temperature of 257° C., overall molar conversion of propylene of 100% and molar selectivity for cumene of 95.5% with respect to the converted propylene.

The reaction products are submitted to suitable treatments to separate the various constituents. More particularly, said products are delivered through pipe 32 to apparatus 13 in which they are expanded with consequent evaporation of about 20% by weight of the liquid. These vapors issuing through pipe 33 are cooled and condensed, and the hydration water of the catalyst is removed in decanter 14 and delivered continuously to the alkylation together with the reagents.

The organic phase is delivered through pipe 35 to apparatus 15, in which propane is removed at the top through pipe 36 at a rate of 505 kg/h.

At the bottom of apparatus 15 there is recovered a liquid stream (19,300 kg/h) consisting essentially of benzene with small amounts of cumene and non-aromatic compounds, which is recycled through pipe 37, excepting a small percentage discharged to keep the content of non-aromatic compounds at low values. The liquid products discharged from the bottom of apparatus 13 are delivered through pipe 34 to apparatus 16, in which impure benzene is recovered at the top at a rate of 56,475 kg/h and, excepting a vented portion, is recycled through pipes 38 and 23 together with the benzene recycled through pipe 37.

The bottom liquid products of apparatus 16 are delivered through pipe 39 to apparatus 17, in which cumene is discharged at the top at a rate of 15,260 kg/h, and is recovered through pipe 40. At the bottom of the column the heavy by-products are discharged at a rate of 440 kg/h through pipe 46. The quantity of said by-products is thus equal to 29 kg for each 1000 kg of cumene.

We claim:

1. A continuous process for the production of cumene by alkylation of benzene with propylene on a solid phosphoric acid catalyst, which comprises:

using two reaction steps in series, the first step being carried out in a plurality of catalyst beds in series and the second step in a catalyst bed having a volume substantially equal to the overall volume of the catalyst beds of the first step;

operating in said first and second steps in a substantially liquid phase, at a temperature of from 170° C. to 270° C. and under a pressure of from 30 to 50 Kg/sq. cm.;

using an overall benzene/propylene molar ratio of from 6:1 to 10:1, continuously delivering the whole of the benzene in the liquid form to the first catalyst bed of the first step, continuously delivering a series of streams of liquid propylene respectively to the first catalyst bed of the first step and, in the form of a cold stream, between each pair of contiguous beds of the first and second steps, in such amounts that the benzene/propylene molar ratio be about 16:1 to 25:1 at the inlet of each individual catalyst bed of the first step, and higher than about 25:1 at the inlet of the catalyst bed of the second step; and recovering cumene from the reaction products discharged from the second step.

2. The process of claim 1, wherein from 2 to 5 catalyst beds are used in the first step.

3. The process of claim 1, wherein three catalyst beds are used in the first step.

4. The process of claim 1, wherein the benzene/propylene molar ratio at the inlet of the second step is of the order of 40:1.

5. The process of claim 1, wherein the temperature of said cold streams of propylene is from 15° to 50° C.

6. The process of claim 1, wherein there is used a space velocity of from 0.3 to 1.4 volumes of liquid reaction medium per volume of catalyst and per hour.

7. The process of claim 6, wherein said space velocity is from 0.4 to 0.9.

8. The process of claim 1, wherein the residence time in the second step is substantially equal to the overall residence time in the first step.

9. The process of claim 1, wherein the increase in temperature along each individual bed is controlled to a value of from about 15° to about 20° C. in the first step, and to a value of about 10° in the second step.

* * * * *